US009408895B2

(12) United States Patent
Fallon (10) Patent No.: US 9,408,895 B2
(45) Date of Patent: *Aug. 9, 2016

(54) METHOD OF TREATING PREGNANCY-INDUCED HYPERTENSION

(71) Applicant: Curemark, LLC, Rye, NY (US)

(72) Inventor: Joan M. Fallon, Bronxville, NY (US)

(73) Assignee: CUREMARK, LLC, Rye, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,385

(22) Filed: Mar. 6, 2015

(65) Prior Publication Data

US 2015/0174220 A1    Jun. 25, 2015

Related U.S. Application Data

(62) Division of application No. 14/037,696, filed on Sep. 26, 2013, which is a division of application No. 12/047,818, filed on Mar. 13, 2008, now Pat. No. 8,658,163.

(51) Int. Cl.
| | | |
|---|---|---|
| *A61K 38/00* | (2006.01) | |
| *A61K 38/54* | (2006.01) | |
| *A61K 36/185* | (2006.01) | |
| *A61K 38/47* | (2006.01) | |
| *A61K 38/48* | (2006.01) | |
| *A61K 38/46* | (2006.01) | |

(52) U.S. Cl.
CPC .............. *A61K 38/54* (2013.01); *A61K 36/185* (2013.01); *A61K 38/465* (2013.01); *A61K 38/47* (2013.01); *A61K 38/48* (2013.01); *A61K 38/4826* (2013.01); *A61K 38/4873* (2013.01); *C12Y 302/01* (2013.01); *C12Y 304/21001* (2013.01); *C12Y 304/21004* (2013.01); *C12Y 304/22002* (2013.01)

(58) Field of Classification Search
None
See application file for complete search history.

(56) References Cited

U.S. PATENT DOCUMENTS

| | | | |
|---|---|---|---|
| 3,002,883 | A | 10/1961 | Butt et al. |
| 3,223,594 | A | 12/1965 | Serge |
| 3,322,626 | A | 5/1967 | D'Argento |
| 3,357,894 | A | 12/1967 | Jose et al. |
| 3,515,642 | A | 6/1970 | Mima et al. |
| 3,574,819 | A | 4/1971 | Gross et al. |
| 3,860,708 | A | 1/1975 | Prout |
| 3,940,478 | A | 2/1976 | Kurtz |
| 4,079,125 | A | 3/1978 | Sipos |
| 4,145,410 | A | 3/1979 | Sears |
| 4,241,046 | A | 12/1980 | Papahadjopoulos et al. |
| 4,280,971 | A | 7/1981 | Wischniewski et al. |
| 4,447,412 | A | 5/1984 | Bilton |
| 4,456,544 | A | 6/1984 | Lupova et al. |
| 4,623,624 | A | 11/1986 | Schultze |
| 4,826,679 | A | 5/1989 | Roy |
| 5,190,775 | A | 3/1993 | Klose |
| 5,250,418 | A | 10/1993 | Moller et al. |
| 5,324,514 | A | 6/1994 | Sipos |
| 5,378,462 | A | 1/1995 | Boedecker et al. |
| 5,436,319 | A | 7/1995 | Kung et al. |
| 5,437,319 | A | 8/1995 | Garuglieri |
| 5,439,935 | A | 8/1995 | Rawlings et al. |
| 5,460,812 | A | 10/1995 | Sipos |
| 5,476,661 | A | 12/1995 | Pillai et al. |
| 5,527,678 | A | 6/1996 | Blaser et al. |
| 5,585,115 | A | 12/1996 | Sherwood et al. |
| 5,607,863 | A | 3/1997 | Chandler |
| 5,648,335 | A | 7/1997 | Lewis et al. |
| 5,674,532 | A | 10/1997 | Atzl et al. |
| 5,686,311 | A | 11/1997 | Shaw |
| 5,750,104 | A | 5/1998 | Sipos |
| 5,776,917 | A | 7/1998 | Blank et al. |
| 5,858,758 | A | 1/1999 | Hillman et al. |
| 5,952,178 | A | 9/1999 | Lapidus et al. |
| 5,958,875 | A | 9/1999 | Longo et al. |
| 5,977,175 | A | 11/1999 | Lin |
| 5,985,891 | A | 11/1999 | Rowe |
| 6,011,001 | A | 1/2000 | Navia et al. |
| 6,013,286 | A | 1/2000 | Klose |
| 6,020,310 | A | 2/2000 | Beck et al. |

(Continued)

FOREIGN PATENT DOCUMENTS

| | | |
|---|---|---|
| CA | 2198317 A1 | 2/1997 |
| CA | 2263703 A1 | 8/1999 |

(Continued)

OTHER PUBLICATIONS

U.S. Appl. No. 14/693,711, filed Apr. 22, 2015, Fallon.
U.S. Appl. No. 14/713,178, filed May 15, 2015, Fallon.
U.S. Appl. No. 14/713,221, filed May 15, 2015, Fallon et al.
U.S. Appl. No. 14/713,242, filed May 15, 2015, Fallon et al.
Fliri, et al. Drug effects viewed from a signal transduction network perspective. J Med Chem. Dec. 24, 2009;52(24):8038-46. doi: 10.1021/jm901001p.
Mizutani, et al. Effects of placental proteases on maternal and fetal blood pressure in normal pregnancy and preeclampsia. Am J Hypertens. Jun. 1996;9(6):591-7.
NIH, "Celiac Disease", National Digestive Diseases Information Clearinghouse: Bethesda, MD, 2008; 12 pages.
Notice of allowance dated Apr. 3, 2015 for U.S. Appl. No. 13/737,225.

(Continued)

*Primary Examiner* — Hope Robinson
(74) *Attorney, Agent, or Firm* — Wilson Sonsini Goodrich & Rosati (57) ABSTRACT

A therapeutic agent for the treatment of toxemia, preeclampsia and eclampsia and a method for preparing the therapeutic agent are disclosed. The therapeutic agent is a stable pharmaceutical preparation containing, but not limited to, digestive/pancreatic enzymes. The therapeutic agent may be manufactured by a variety of encapsulation technologies. Delivery of the therapeutic agent may be made orally, through injection, by adherence of a medicated patch or by other methods. Further, a method of using the presence of chymotrypsin in the maternal GI tract as a biomarker, to determine the likelihood of developing preeclampsia, a pregnancy induced hypertension, and eclampsia/toxemia is disclosed.

12 Claims, 4 Drawing Sheets

(56) References Cited

U.S. PATENT DOCUMENTS

| | | |
|---|---|---|
| 6,020,314 A | 2/2000 | McMichael |
| 6,096,338 A | 8/2000 | Lacy et al. |
| 6,149,585 A | 11/2000 | Gray |
| 6,153,236 A | 11/2000 | Wu et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,251,478 B1 | 6/2001 | Pacifico et al. |
| 6,261,602 B1 | 7/2001 | Calanchi et al. |
| 6,261,613 B1 | 7/2001 | Narayanaswamy et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,632,429 B1 | 10/2003 | Fallon |
| 6,660,831 B2 | 12/2003 | Fallon |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,613,918 B2 | 12/2013 | Fallon |
| 8,921,054 B2 | 12/2014 | Fallon |
| 8,980,252 B2 | 3/2015 | Fallon |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0090653 A1 | 7/2002 | Fallon |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0258599 A1 | 11/2006 | Childers |
| 2006/0259995 A1 | 11/2006 | Cayouette et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0187525 A1 | 8/2008 | Porubcan |
| 2008/0199448 A1 | 8/2008 | Ross et al. |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0110674 A1 | 4/2009 | Loizou |
| 2009/0117180 A1 | 5/2009 | Ortenzi et al. |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |

(56) References Cited

U.S. PATENT DOCUMENTS

| | | |
|---|---|---|
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon |
| 2012/0027848 A1 | 2/2012 | Fallon |
| 2012/0070504 A1 | 3/2012 | Fallon |
| 2012/0114562 A1 | 5/2012 | Fallon |
| 2012/0114626 A1 | 5/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2012/0258149 A1 | 10/2012 | Fallon et al. |
| 2013/0059001 A1 | 3/2013 | Fallon |
| 2013/0095152 A1 | 4/2013 | Fallon et al. |
| 2013/0113129 A1 | 5/2013 | Fallon et al. |
| 2014/0161787 A1 | 6/2014 | Fallon |
| 2014/0348881 A1 | 11/2014 | Fallon |
| 2015/0023944 A1 | 1/2015 | Fallon |
| 2015/0140550 A1 | 5/2015 | Fallon |
| 2015/0147308 A1 | 5/2015 | Fallon et al. |
| 2015/0150955 A1 | 6/2015 | Fallon et al. |
| 2015/0174219 A1 | 6/2015 | Fallon |
| 2015/0246104 A1 | 9/2015 | Fallon et al. |
| 2015/0246105 A1 | 9/2015 | Fallon et al. |
| 2015/0273030 A1 | 10/2015 | Fallon |
| 2015/0335589 A1 | 11/2015 | Fallon et al. |

FOREIGN PATENT DOCUMENTS

| | | |
|---|---|---|
| CN | 1031562 A | 3/1989 |
| CN | 1329923 A | 1/2002 |
| DE | 4332985 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1335706 B1 | 4/2005 |
| EP | 1019072 B1 | 5/2005 |
| EP | 1604677 A1 | 12/2005 |
| EP | 1931317 B1 | 6/2008 |
| EP | 2258837 A1 | 12/2010 |
| GB | 669782 A | 4/1952 |
| GB | 2347742 A | 9/2000 |
| JP | 62230714 A | 10/1987 |
| JP | H 04-364119 A | 12/1992 |
| RU | 2356244 C1 | 5/2009 |
| TW | 310277 B | 7/1997 |
| WO | WO 84/02846 A1 | 8/1984 |
| WO | WO 90/02562 A1 | 3/1990 |
| WO | WO 94/19005 A1 | 9/1994 |
| WO | WO 95/22344 A1 | 8/1995 |
| WO | WO 97/32480 A1 | 9/1997 |
| WO | WO 98/22499 A2 | 5/1998 |
| WO | WO 98/22499 A3 | 7/1998 |
| WO | WO 98/52593 A1 | 11/1998 |
| WO | WO 99/64059 A2 | 12/1999 |
| WO | WO 00/09142 A1 | 2/2000 |
| WO | WO 99/64059 A3 | 3/2000 |
| WO | WO 00/21504 A1 | 4/2000 |
| WO | WO 01/27612 A2 | 4/2001 |
| WO | WO 01/43764 A2 | 6/2001 |
| WO | WO 01/45835 A1 | 6/2001 |
| WO | WO 01/27612 A3 | 10/2001 |
| WO | WO 01/43764 A3 | 11/2001 |
| WO | WO 02/14537 A2 | 2/2002 |
| WO | WO 02/14537 A3 | 5/2002 |
| WO | WO 02/051352 A2 | 7/2002 |
| WO | WO 02/051436 A2 | 7/2002 |
| WO | WO 03/051345 A2 | 6/2003 |
| WO | WO 03/059088 A1 | 7/2003 |
| WO | WO 2004/060074 A1 | 7/2004 |
| WO | WO 2005/115445 A1 | 12/2005 |
| WO | WO 2006/031554 A2 | 3/2006 |
| WO | WO 2006/044529 A1 | 4/2006 |
| WO | WO 2006/031554 A3 | 9/2006 |
| WO | WO 2007/002572 A2 | 1/2007 |
| WO | WO 2007/074454 A2 | 7/2007 |
| WO | WO 2007/147714 A1 | 12/2007 |
| WO | WO 2008/021987 A2 | 2/2008 |
| WO | WO 2008/102264 A2 | 8/2008 |
| WO | WO 2009/114757 A2 | 9/2009 |
| WO | WO 2009/155689 A1 | 12/2009 |
| WO | WO 2010/002972 A1 | 1/2010 |
| WO | WO 2010/025126 A1 | 3/2010 |
| WO | WO 2010/080830 A1 | 7/2010 |
| WO | WO 2010/080835 A1 | 7/2010 |
| WO | WO 2010/120781 A1 | 10/2010 |
| WO | WO 2011/000924 A1 | 1/2011 |
| WO | WO 2011/114225 A1 | 9/2011 |

OTHER PUBLICATIONS

Notice of allowance dated Apr. 10, 2015 for U.S. Appl. No. 13/144,290.
Notice of allowance dated Apr. 14, 2015 for U.S. Appl. No. 13/144,286.
Office action dated Apr. 6, 2015 for U.S. Appl. No. 14/493,734.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office action dated Apr. 27, 2015 for U.S. Appl. No. 12/054,343.
Office action dated May 6, 2015 for U.S. Appl. No. 12/493,122.
Office action dated May 7, 2015 for U.S. Appl. No. 13/705,763.
Office action dated May 27, 2015 for U.S. Appl. No. 13/502,989.
Office action dated Jun. 3, 2015 for U.S. Appl. No. 13/002,136.
Office action dated Jul. 17, 2015 for U.S. Appl. No. 13/733,873.
Richards, et al. Diagnosis, management, and treatment of Alzheimer disease: a guide for the internist. Arch Intern Med. Apr. 26, 1999;159(8):789-98.
Swayne, et al. Pathobiology of H5N2 Mexican avian influenza virus infections of chickens. Vet Pathol. Nov. 1997;34(6):557-67.
U.S. Appl. No. 14/528,715, filed Oct. 30, 2014, Fallon.
U.S. Appl. No. 14/612,580, filed Feb. 3, 2015, Fallon et al.
U.S. Appl. No. 14/612,604, filed Feb. 3, 2015, Fallon et al.
U.S. Appl. No. 14/639,425, filed Mar. 5, 2015, Fallon.
ABCnews. Changing Face of Autism: Numbers Rise as More Behaviors Included. ABCnews. Nov. 01, 2007.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.

(56) References Cited

OTHER PUBLICATIONS

Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.
Ang, et al. Biological role and regulation of the universally conserved heat shock proteins. J Biol Chem. Dec. 25, 1991;266(36):24233-6.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
ASH. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barlow. A comparison of the blood pressure, kidney volume and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol Jun. 2003;90(6 Suppl 3):84-9.
Belmonte et al. Fragile X syndrome and autism at the intersection of genetic and neural networks. Nat Neurosci. Oct. 2006; 9(10):1221-5 (abstract only).
Berg, et al. Section 10.5 Many Enzymes Are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.
Birnbaum, et al. Heat shock or stress proteins and their role as autoantigens in multiple sclerosis. Ann N Y Acad Sci. Dec. 19, 1997;835:157-67. Abstract only.
Blackmer. Parkinson disease: treatment and medication. Mar. 10, 2009., retrieved from the internet on Sep. 15, 2009, http://emedicine.medscape.com/article/312519-treatment.
Blog. Acid Phosphatase Research (blog). Acid-phosphatase.blogspot.com. 2008.
Bode et al. Usefulness of a simple photometric determination of chymotrypsin activity in stools—results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borowitz, et al. Use of pancreatic enzyme supplements for patients with cystic fibrosis in the context of fibrosing colonopathy. Consensus Committee. J Pediatr. Nov. 1995;127(5):681-4.
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Brudnak et al. Enzyme-based therapy for autism spectrum disorders—is it worth another look? Med Hypoth. 2002; 58:422-428.

(56) References Cited

OTHER PUBLICATIONS

Bruhat, et al Amino acid limitation induces expression of CHOP, a CCAAT/enhancer binding protein-related gene, at both transcriptional and post-transcriptional levels. J Biol Chem. Jul. 11, 1997;272(28):17588-93.

Campbell et al. A genetic variant that disrupts MET transcription is associated with autism. Proc Natl Acad Sci USA. 2006; 103(45):16834-16839.

Campbell, et al. Distinct genetic risk based on association of MET in families with co-occurring autism and gastrointestinal conditions. Pediatrics. Mar. 2009;123(3):1018-24.

Carlton. Autism and malnutrition: the milk connection. Retrieved from the internet on Feb. 18, 2008, http://www.mercola.com/2004/autism_malnutrition.htm.

Caronna, et al. Autism spectrum disorders: clinical and research frontiers. Arch Dis Child. Jun. 2008;93(6):518-23.

Carroccio, et al. Secondary impairment of pancreatic function as a cause of severe malabsorption in intestinal giardiasis: a case report. Am J Trop Med Hyg. Jun. 1997;56(6):599-602.

Carroccio, et al. Secretin-cerulein test and fecal chymotrypsin concentration in children with intestinal giardiasis. Int J Pancreatol. Oct. 1993;14(2):175-80.

Cassidy, et al. A new concept for the mechanism of action of chymotrypsin: the role of the low-barrier hydrogen bond. Biochemistry. Apr. 15, 1997;36(15):4576-84.

CDC. Attention-Deficit/Hyperactivity Disorder (ADHD). Www.cdc.org. 2005.

CDC. Autism Information Center/FAQs. Dept of Health and Human Services/CDC. Jan. 30, 2008.

Chen, et al. Identification of two lysosomal membrane glycoproteins. J Cell Biol. Jul. 1985;101(1):85-95.

Chen, et al. Lysine 43 is trimethylated in subunit C from bovine mitochondrial ATP synthase and in storage bodies associated with batten disease. J Biol Chem. May 21, 2004;279(21):21883-7.

Cichoke, et al. The complete book of enzyme therapy. Penguin. 1998: 39, 42, 47, 50, and 53.

Claud, et a. Hypothesis: inappropriate colonization of the premature intestine can cause neonatal necrotizing enterocolitis. FASEB J. Jun. 2001;15(8):1398-403.

Corring, et al. Development of digestive enzymes in the piglet from birth to 8 weeks. I. Pancreas and pancreatic enzymes. Nutr Metab. 1978;22(4):231-43.

Couet, et al. Identification of peptide and protein ligands for the caveolin-scaffolding domain. Implications for the interaction of caveolin with caveolae-associated proteins. J Biol Chem. Mar. 7, 1997;272(10):6525-33.

Coyle. Treating the Negative Symptoms of Schizophrenia: An Expert Interview with Joseph Coyle, MD. www.narsad.org/?q=node/438/latest-research. 2006.

Craig, et al. Heat shock proteins: molecular chaperones of protein biogenesis. Microbiol Rev. Jun. 1993;57(2):402-14.

Croonenberghs, et al. Peripheral markers of serotonergic and noradrenergic function in post-pubertal, caucasian males with autistic disorder. Neuropsychopharmacology. Mar. 2000;22(3):275-83.

Cruse et al. Illustrated dictionary of immunology. CRC Press, New York. 1995.

Cuervo, et al. Cathepsin A regulates chaperone-mediated autophagy through cleavage of the lysosomal receptor. EMBO J. Jan. 2, 2003;22(1):47-59.

Dajcs, et al. Lysostaphin is effective in treating methicillin-resistant *Staphylococcus aureus* endophthalmitis in the rabbit. Curr Eye Res. Jun. 2001;22(6):451-7.

Darman. An introduction to alternative medicine for psychiactric conditions. Oct. 22, 2007, retrieved on Sep. 18, 2009, http://web.archive.org/web/20071022104238/http://altp[therapies4bipolar.info/ortho/html.

Dawe, et al. The chakragati mouse: a mouse model for rapid in vivo screening of antipsychotic drug candidates. Biotechnol J. Nov. 2007;2(11):1344-52.

Dawn. Autism: the Latest Prevalence Rates in USA—Now 1 in 175. Disabled Women's Network Ontario. Dawn.thot.net/autism2.html. 2006.

Dawson lab. Research Projects in Synthetic Protein Chemistry. 2005; 1-2.

Derwent. English abstract for RU 2286785 Nov. 10, 2006. Downloaded from the Derwent file Jul. 13, 2011.

Diaz-Hernandez, et al. Neuronal induction of the immunoproteasome in Huntington's disease. J Neurosci. Dec. 17, 2003;23(37):11653-61.

Digestive Enzyme Wikipedia. Retrieved from the internet Sep. 10, 2009, http://en.wikipedia.org/wiki/Digestive_enzyme.

Ding, et al. Proteasome inhibition in oxidative stress neurotoxicity: implications for heat shock proteins. J Neurochem. May 2001;77(4):1010-7.

Dobbs et al. Link between helicobacter pylori infection and idiopathic parkinsonism. Medical Hypothsis. 2000; 55(2):93-98.

Dockter et al. Determination of chymotrypsin in the feces by a new photometric method. Padiatr Padol. 1985; 20(3):257-265.

Dupiereux, et al. Creutzfeldt Jakob, Parkinson, lewy body dementia and Alzheimer diseases: from diagnosis to therapy. Cent Nerv Syst Agents Med Chem. Mar. 2009;9(1):2-11.

Edelson, et al. 3-Cyclohexene-1-glycine, an Isoleucine Antagonist. J. Am. Chem. Soc. 1958; 80(11):2698-2700.

Elkashef, et al. Biological markers of cocaine addiction: implications for medications development. Addict Biol. Jun. 2003;8(2):123-39.

Elphick, et al. Impaired luminal processing of human defensin-5 in Crohn's disease: persistence in a complex with chymotrypsinogen and trypsin. Am J Pathol. Mar. 2008;172(3):702-13.

Ethridge, et al. Acute pancreatitis results in induction of heat shock proteins 70 and 27 and heat shock factor-1. Pancreas. Oct. 2000;21(3):248-56.

Fafournoux, et al. Amino acid regulation of gene expression. Biochem J. Oct. 1, 2000;351(Pt 1):1-12.

Fallingborg, et al. Measurement of gastrointestinal pH and regional transit times in normal children. J Pediatr Gastroenterol Nutr. Aug. 1990;11(2):211-4.

Fallon. Could one of the most widely prescribed antibiotics amoxicillin/clavulanate "augmentin" be a risk factor for autism? Med Hypotheses. 2005;64(2):312-5.

Fernell, et al. No evidence for a clear link between active intestinal inflammation and autism based on analyses of faecal calprotectin and rectal nitric oxide. Acta Paediatr. Jul. 2007;96(7):1076-9.

Filipek et al. The screening and diagnosis of autistic spectrum disorders. J. of Autism and Dev Disorders. 1999; 29(6).

Final Office Action dated Jan. 3, 2012 for U.S. Appl. No. 10/681,018.

Final Office Action dated Jan. 26, 2012 for U.S. Appl. No. 12/487,864.

Final Office Action dated Nov. 8, 2011 for U.S. Appl. No. 12/054,343.

Final Office Action dated Nov. 8, 2011 for U.S. Appl. No. 12/786,739.

Final Office Action dated Nov. 9, 2010 for U.S. Appl. No. 09/990,909.

Final Office Action dated Feb. 14, 2011 for U.S. Appl. No. 12/049,613.

Final Office Action dated Feb. 27, 2009 for U.S. Appl. No. 11/555,697.

Final Office Action dated Mar. 13, 2009 for U.S. Appl. No. 11/232,180.

Final Office Action dated Mar. 17, 2008 for U.S. Appl. No. 10/681,018.

Final Office Action dated Apr. 28, 2009 for U.S. Appl. No. 10/681,018.

Final Office Action dated May 11, 2010 for U.S. Appl. No. 11/555,697.

Final Office Action dated Jun. 25, 2008 for U.S. Appl. No. 11/213,255.

Final Office Action dated Jul. 2, 2010 for U.S. Appl. No. 12/046,252.

Final Office Action dated Jul. 27, 2004 for U.S. Appl. No. 09/990,909.

Finegold et al. Gastrointestinal microflora studies in late-onset autism. Clinical Infectious Diseases. 2002; 35(1):S6-S15.

(56) References Cited

OTHER PUBLICATIONS

Fitzsimmons, et al. High-dose pancreatic-enzyme supplements and fibrosing colonopathy in children with cystic fibrosis. N Engl J Med. May 1, 1997;336(18):1283-9.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of giardia lamblia, entamoeba histolytica/ entamoeba dispar, and cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr., et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Giglio, et al. Failure to thrive: the earliest feature of cystic fibrosis in infants diagnosed by neonatal screening. Acta Paediatr. Nov. 1997;86(11):1162-5.
Goff, et al. Production of abnormal proteins in *E. coli* stimulates transcription of lon and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Thl- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
HEALTH.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
Hitti. Allergy, celiac disease, and ileal lymphonodular. WebMD. 2005. 1-2.
Horvath et al. Improved social and language skills after secretin administration in patients with autistic spectrum disorders. Journal of the Association for Academic Minority Physicians. Jan. 1998; 9(1):9-15.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al Thimerosal neurotoxicity is associated with glutathione depletion: protection with glutathione precursors. Neurotoxicology. 2004; 26(1):1-8.
Jenkins, et al. Management of gastroenteritis. Archives of Disease in Childhood. 1990; 65:939-941.
Juhl. Fibromyalgia and the serotonin pathway. Altera Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.
Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Kearney, et al. Global burden of hypertension: analysis of worldwide data. Lancet. Jan. 15-21, 2005;365(9455):217-23. Abstract only.
Knivsberg, et al. A randomised, controlled study of dietary intervention in autistic syndromes. Nutr Neurosci. Sep. 2002;5(4):251-61.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koster et al. Evidence based medicine and extradigestive manifestations of helocobacter pylori. Acta Gastro-Enterologica Belgica. 2000; 63(4):388-392.
Kujoth, et al. Mitochondrial DNA mutations, oxidative stress, and apoptosis in mammalian aging. Science. Jul. 15, 2005;309(5733):481-4.
Lashkari, et al. Williams-Beuren syndrome: An update and review for the primary physician. Clinical Pediatrics. 1999; 38(4):189-208.
Layer et al. Pancreatic enzyme replacement therapy. Current Gastroenterology Reports. 2001; 3:101-108.

(56) References Cited

OTHER PUBLICATIONS

Levy, et al. Relationship of dietary intake to gastrointestinal symptoms in children with autistic spectrum disorders. Biol Psychiatry. Feb. 15, 2007;61(4):492-7.

Leyfer, et al. Comorbid psychiatric disorders in children with autism: interview development and rates of disorders. J Autism Dev Disord. Oct. 2006;36(7):849-61.

Lieberman. Pharmaceutical Dosage Forms. vol. 2: Disperse Systems. New York Marcel Dekker, Inc. 1996; 243-258.

Lipase 30, Technical Data sheet, 1 page, Scientific Protein Laboratories LLC Jun. 13, 2005.

Liyanage, et al. Bioavailability of iron from micro-encapsulated iron sprinkle supplement. Food and Nutrition bulletin. 2002; 23(3):133-137.

Lloyd. Lysosome membrane permeability: implications for drug delivery. Adv Drug Deliv Rev. Mar. 30, 2000;41(2):189-200.

Loh, et al. Highly tolerated amino acid substitutions increase the fidelity of *Escherichia coli* DNA polymerase I. J Biol Chem. Apr. 20, 2007;282(16):12201-9.

Lord, et al. Diagnostic Instruments in Autistic Spectrum Disorders. info.med.yale.edu. 2005; 11:730-771.

Luedtke, et al. Cathepsin A is expressed in a cell- and region-specific manner in the testis and epididymis and is not regulated by testicular or pituitary factors. J Histochem Cytochem. Aug. 2000;48(8):1131-46.

MacFabe, et al. Neurobiological effects of intraventricular propionic acid in rats: possible role of short chain fatty acids on the pathogenesis and characteristics of autism spectrum disorders. Behav Brain Res. 2006;176(1):149-69.

MacReady. Parkinson's Diseasne Treatment: what you should know. Retrieved from the internet on Sep. 15, 2009, http://www.everydayhealth.com/parkinsons-disease-treatment-overview.aspx.

Mannino, et al. Surveillance for asthma—United States, 1960-1995. MMWR CDC Surveill Summ. Apr. 24, 1998;47(1):1-27.

Marczewska et al. Protein intake in parkinsonian using the EPIC food frequency questionnaire. Mov Diord. Aug. 2006; 21(8):1229-1231.

Marlicz et al. Determination of chymotrypsin in the stool in the diagnosis of chronic pancreatitis. Wiadomosci lekarskie. 1988; 41(11):704-707. (in Polish with English abstract/summary).

Marsh. Neuropsychiatric aspects of parkinson's disease. Psychosomatics. 2000; 41(1):15-23.

Martin, et al. A rapid and sensitive spectrophotometric method for the assay of chymotrypsin. Biol Chem. Feb. 1959;234(2):294-8.

Maurin, et al. Cellular adaptation to amino acid availability: mechanisms involved in the regulation of gene expression. 2006; 319-326.

Mayo Clinic Staff. Autism. Retrieved from internet Mar. 10, 2008, http://www.mayoclinic.com/health/autism/DS00348DSECTION=2.

Mayo Clinic Staff. Bipolar disorder. Jan. 4, 2008, http://www.mayoclinic.com/health/bipolardisorder/DS00356/DSECTION=symptoms.

Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.

Mayo Clinic Staff. Oppositional defiant disorder. Dec. 19, 2007, http://www.mayoclinic.com/health/oppositional-defiant-disorder/DS00630/DSECTION=symptoms.

McAlonan, et al. Brain anatomy and sensorimotor gating in Asperger's syndrome. ain. Jul. 2002;125(Pt 7):1594-606.

McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.

McCracken, et al. Risperidone in children with autism and serious behavioral problems. N Engl J Med. Aug. 1, 2002;347(5):314-21.

Medsafe. Data sheet for alpha-lactose, Jul. 21, 2008, http://www.medsafe.govt.nz/Profs/Datasheet/a/Alphalactulosesyrup.htm.

Merck. Autism, Merck manual online medical library home addition, retrieved from the internet Mar. 10, 2008, http://www.mercl.com/mmhge/sec23/ch286/ch286b.html.

MeSH browser. "Child Development Disorders, Pervasive," and "Attention Deficit and Disruptive Behavior Disorders," National Library of medicine. 2001, http://www.nlm.nih.gov/mesh/2002/Mbrowser.html.

Meyer-Lindenberg, et al. Neural mechanisms in Williams syndrome: a unique window to genetic influences on cognition and behavior. Nat. Rev. Neurosci. 2006; 7(5):380-93.

Michell et al. Biomarkers and parkinson's disease. Brain. 2004; 127(8):1693-1705.

Minamino, et al. Vascular cell senescence: contribution to atherosclerosis. Circ Res. Jan. 5, 2007;100(1):15-26.

Ming, et al. Autism spectrum disorders: concurrent clinical disorders. J Child Neurol. Jan. 2008;23(1):6-13.

Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.

Mononen, et al. Aspartylglycosaminuria in the Finnish population: identification of two point mutations in the heavy chain of glycoasparaginase. Proc Natl Acad Sci U S A. Apr. 1, 1991;88(7):2941-5.

Munasinghe et al. Digestive enzyme supplementation for autism spectrum disorders: a double-blind randomized controlled trial. J Autism Dev Disord. Sep. 2010;40(9):1131-8. Abstract only.

Nachaegari et al. Coprocessed excipients for solid dosage forms. Pharmaceutical Technology. 2004; p. 52, 54, 56 ,58, 60, 64.

Nagamoto. Jacobson: Psychiatric Secrets, 2nd ed. 2001. Ch 28 Antipsychotic meds.

Neuer, et al. The role of heat shock proteins in reproduction. Hum Reprod Update. Mar.-Apr. 2000;6(2):149-59.

Nevo et al. Acute immune polyneuropathies: correlations of serum antibodies to campylobacter jejuni and helicobacter pylon with antigm antibodies and clinical patterns of disease. J of Inf diseases. 1997; 175(S2):S154-6.

NINDS Dysautonimia Information Page, retrieved from the internet Sep. 10, 2009, http://www.ninds.nih.gov/disorders/dysautonomia/dysautonomia.htm.

NINDS Guillain-Barre Syndrome Information Page, retrieved from the internet Sep. 15, 2009, http://www.ninds.nih.gov/disorders/gbs/gbs.htm.

Notice Non-Compliant Amendment dated Jun. 19, 2009 for U.S. Appl. No. 11/232,180.

Notice Non-responsive Amendment dated Sep. 22, 2008 for U.S. Appl. No. 11/232,180.

Notice of Allowance dated Feb. 17, 2012 for U.S. Appl. No. 10/681,018.

Notice of Allowance dated Mar. 21, 2012 for U.S. Appl. No. 12/487,864.

Notice of Allowance dated Apr. 15, 2011 for U.S. Appl. No. 12/487,868.

Notice of Allowance dated Apr. 29, 2011 for U.S. Appl. No. 12/046,402.

Notice of Allowance dated May 23, 2011 for U.S. Appl. No. 09/990,909.

Notice of Allowance dated Jun. 27, 2011 for U.S. Appl. No. 12/238,415.

Notice of Allowance dated Jun. 28, 2011 for U.S. Appl. No. 12/487,868.

Notice of Allowance dated Jun. 30, 2011 for U.S. Appl. No. 09/990,909.

Notice of allowance dated Jul. 3, 2012 for U.S. Appl. No. 13/271,783.

Notice of Allowance dated Jul. 8, 2011 for U.S. Appl. No. 12/046,402.

Notice of Allowance dated Aug. 8, 2011 for U.S. Appl. No. 12/426,794.

Notice of Allowance dated Sep. 20, 2011 for U.S. Appl. No. 12/283,090.

Notice of Non-Complaint Amendment dated Jun. 2, 2008 for U.S. Appl. No. 12/046,252.

(56) References Cited

OTHER PUBLICATIONS

Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
Office action dated Jan. 12, 2012 for U.S. Appl. No. 12/047,818.
Office Action dated Feb. 1, 2012 for U.S. Appl. No. 12/493,122.
Office Action dated Mar. 5, 2012 for U.S. Appl. No. 12/535,676.
Office Action dated Mar. 19, 2012 for U.S. Appl. No. 13/204,881.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office Action dated Apr. 5, 2012 for U.S. Appl. No. 11/555,697.
Office Action dated Apr. 9, 2012 for U.S. Appl. No. 13/208,963.
Office Action dated Apr. 27, 2011 for U.S. Appl. No. 10/681,018.
Office Action dated Apr. 28, 2011 for U.S. Appl. No. 12/283,090.
Office Action dated May 24, 2011 for U.S. Appl. No. 12/487,864.
Office action dated Jun. 13, 2012 for U.S. Appl. No. 12/493,122.
Office action dated Jun. 27, 2012 for U.S. Appl. No. 12/493,147.
Office action dated Jun. 29, 2011 for U.S. Appl. No. 11/555,697.
Office action dated Jul. 11, 2012 for U.S. Appl. No. 12/573,353.
Office action dated Jul. 18, 2012 for U.S. Appl. No. 12/047,818.
Office action dated Aug. 13, 2012 for U.S. Appl. No. 13/208,963.
Office action dated Sep. 13, 2012 for U.S. Appl. No. 13/481,087.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 25, 2012 for U.S. Appl. No. 13/144,286.
Office action dated Oct. 25, 2012 for U.S. Appl. No. 13/144,290.
Office Action dated Oct. 5, 2010 for U.S. Appl. No. 12/046,402.
Office Action dated Nov. 14, 2007 for U.S. Appl. No. 11/213,255.
Office Action dated Nov. 15, 2010 for U.S. Appl. No. 12/238,415.
Office Action dated Nov. 25, 2009 for U.S. Appl. No. 11/232,180.
Office Action dated Nov. 26, 2001 for U.S. Appl. No. 09/466,559.
Office action dated Dec. 6, 2012 for U.S. Appl. No. 13/002,136.
Office action dated Dec. 15, 2011 for U.S. Appl. No. 12/493,147.
Office Action dated Dec. 19, 2005 for U.S. Appl. No. 10/730,567.
Office Action dated Dec. 22, 2006 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.

Owley, et al. Multisite, double-blind, placebo-controlled trial of porcine secretin in autism. J Am Acad Child Adolesc Psychiatry. Nov. 2001;40(11):1293-9.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Parisi et al. Evaluation of new rapid commercial enzyme immunoassay for detection of crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Perman et al. Role of ph in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.

(56) References Cited

OTHER PUBLICATIONS

Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Rider, et al. Perspective of biochemical research in the neuronal ceroid-lipofuscinosis. Am J Med Genet. Feb. 15, 1992;42(4):519-24.
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Rubenstein, et al. Model of autism: increased ratio of excitation/inhibition in key neural systems. Genes Brain Behav. Oct. 2003;2(5):255-67.
Sandler et al. Short term benefit from oral vancomycin treatment of regressive-onset autism. J of Child Neuro. 2000; 15(7):42-435.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schneider, et al. Oral human immunoglobulin for children with autism and gastrointestinal dysfunction: a prospective, open-label study. J Autism Dev Disord. Nov. 2006;36(8):1053-64.
Schreck, et al. Food preferences and factors influencing food selectivity for children with autism spectrum disorders. Res Dev Disabil. 2005;27(4):353-63.
Schumann. Medical, nutritional and technological properties of lactulose. An update. Eur J Nutr. Nov. 2002;41 Suppl 1:I17-25.
Seneca et al. Enhancement of brain 1-dopa concetration with a-chymotrypsm. J American Geriatrics Society. 1973; 256-258. Abstract only.
Settembre, et al. A block of autophagy in lysosomal storage disorders. Hum Mol Genet. Jan. 1, 2008;17(1):119-29.
Shaul. Report to the Chairman and Ranking Minority Member, Subcommittee on Human Rights and Wellness, Committee on Government Reform, House of Representatives. GEO. Jan. 2005. 1-40.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity Trends Immunol. Dec. 2007;28(12):541-50.
Sillanaukee, et al. Improved diagnostic classification of alcohol abusers by combining carbohydrate-deficient transferrin and gamma-glutamyltransferase. Clin Chem. Apr. 2001;47(4):681-5.
Singh, et al. Plasma increase of interleukin-12 and interferon-gamma. Pathological significance in autism. J Neuroimmunol. May 1996;66(1-2):143-5.
Skeels et al. Crytosporidium infection in Oregon public health clinic patients 1985-88: the value of statewide laboratory surveillance. AJPH. 1990; 80(3):305-308.
Smith, et al. Fecal chymotrypsin and trypsin determinations. Canadian Medical Association Journal. 1971; 104(8):691-4 and 697.
Statemaster. Number of Children with Autism (most recent w/graph) by state. Statemaster.com Jul. 14, 2003.
Statemaster. Number of Children with Autism (most recent) by state. Statemaster.com Jul. 14, 2008.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Supplemental Amendment and Response dated Jun. 8, 2010 to Restriction Requirement dated Oct. 7, 2009 for U.S. Appl. No. 12/283,090.
Tager-Flusberg, et al. Language disorders: autism and other pervasive developmental disorders. Pediatr Clin North Am. Jun. 2007;54(3):469-81, vi.
The Alzheimer's Association. Basics of Alzheimer's Disease. 2005, 32 pages. http://www.alz.org/national/documents/brochure_Basicsofalz_low/pdf.
Thefreedictionary. Term Sprinkles Www.thefreedictionary.com. Accessed Nov. 2, 2011. 1 page.
Thomas, et al. Defective protein folding as a basis of human disease. Trends Biochem Sci. Nov. 1995;20(11):456-9.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Tsang et al. Extragastroduodenal conditions associated with Heliobacter pylori infection. Hong Kong Medical Journal. 1999; 5(2):169-174.
Uhlmann, et al. Potential viral pathogenic mechanism for new variant inflammatory bowel disease. Mol Pathol. Apr. 2002;55(2):84-90.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Vojdani, et al. Antibodies against CNS antigens in autism: Possible cross-reaction with dietary proteins and infectious agent antigens. Neuropsychiatric Disorders and Infection. 2004; 19:171-186.

(56) References Cited

OTHER PUBLICATIONS

Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. Autistic enterocolitis: is it a histopathological entity? Histopathology. 2006; 1-5.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
Weintraub, et al. Morphometric studies of pancreatic acinar granule formation in NCTR-Balb/c mice. J Cell Sci. May 1992;102 ( Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Wisniewski, et al. Therapeutic approaches for prion and Alzheimer's diseases. FEBS J. Aug. 2007;274(15):3784-98. Epub Jul. 6, 2007.
Wohlman et al. Enhancement of drug activity by chymotrypsin, penicillin penetration into granulomatous sesions and inflammatory fluids. Cellular and Molecular Life Sciences. 1969; 25(9):953-954.
Woodward et al. Ischaemic enterocolitis complicating aidiopathic dysatuonomia. Gut. 1998; 43:285-287.
YAHOO!.com. Who is affected by Parkinson's disease. Yahoo! Health. Jul. 14, 2008.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
Zhang et al. Lactulose-mannitol intestinal permeability test in children with diarrhea caused by rotavirus abd cryptosporidium. J of Pediatric Gastro & Nutrition. 2000; 31(1):16-21.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Bray, et al. Effect of dietary protein content on weight gain, energy expenditure, and body composition during overeating. A randomized controlled trial. JAMA. Jan. 4, 2012; 307(1):47-55.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Carroccio, et al. Pancreatic enzyme therapy in childhood celiac disease. A double-blind prospective randomized study. Dig Dis Sci. Dec. 1995;40(12):2555-60.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Childhood Autism Rating Scale (CARS), Wikipedia, downloaded May 5, 2014.
Cichoke. Celiac disease. The complete book of enzyme therapy. Penguin. New York, NY. 1999; 174-177.
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Creon. Full prescribing information. Last edited Mar. 2013. Abbvie Inc 2012. www.rxabbvie.com/pdf/creon_PI.pdf.
Curemark press release. Curemark Receives Investigational New Drug Clearance for CM-AT for Autism. Mar. 26, 2009. http://www.medicalnewstoday.com/releases/143723.php.
Digestive Enzyme Preparation: Pancreatin listed in Japanese Pharmacopoeia, Aug. 2008, <URL:http://database.japic.or.jp/pdf/newPINS/00009938.pdf> (in Japanese with English translation).
Eaves, et al. The criterion-related validity of the Childhood Autism Rating Scale and the Autism Behavior Checklist. J Abnorm Child Psychol. Oct. 1993;21(5):481-91. abstract only.
eMedExpert, Antibiotics:Cephalosporins, Available online at: www.emedexpert.com/compare/ cephalosporins.shtml, available as early as Jun. 2, 2007 per Internet Archive Wayback Machine.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
GM Chemie 2010 "Products: Hypromellose Phthalate" accessed from www.gmchemie.com on Sep. 22, 2014.
Information of Papain from Worthington Enzymes webpage http://www.worthington-biochem.com/pap/default.html Downloaded Jan. 17, 2013.
International preliminary report on patentability dated Jul. 17, 2014 for PCT/US2013/020183.
International search report and written opinion dated Feb. 21, 2013 for PCT/US2013/020183.
International search report and written opinion dated Aug. 27, 2013 for PCT/US2013/043444.
International search report and written opinion dated Nov. 12, 2012 for PCT/US2012/034489.
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Krishnaswami, et al. A systematic review of secretin for children with autism spectrum disorders. Pediatrics. May 2011;127(5):e1322-5. doi: 10.1542/peds.2011-0428. Epub Apr. 4, 2011.

(56) References Cited

OTHER PUBLICATIONS

Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
MacDonald. Thyrotoxicosis treated with pancreatic extract and iodine. Lancet. 1943; 244(6251):788.
Merriam-Webster 2014 "Definition: Precipitate" accessed from www.mirriam-webster.com on Sep. 22, 2014.
Millipore EMD catalog (online) Papain, unit definition, EMD Millipore Corp, 2013. Downloaded May 13, 2013.
Mitsui, et al. Role of aminopepridases in the blood pressure regulation. Biological and Pharmaceutical Bulletin of Japan, Pharmaceutical Sociey of Japan. 2004; 27(6):768-771.
Munasinghe et al. Digestive enzyme supplementation for autism spectrum disorders: a double-blind randomized controlled trial. J Autism Dev Disord. Sep. 2010;40(9):1131-8.
Notice of allowance dated Jan. 2, 2014 for U.S. Appl. No. 13/204,881.
Notice of allowance dated Feb. 2, 2015 for U.S. Appl. No. 13/926,822.
Notice of allowance dated Feb. 20, 2015 for U.S. Appl. No. 12/386,051.
Notice of allowance dated Feb. 27, 2015 for U.S. Appl. No. 14/037,696.
Notice of Allowance dated May 29, 2013 for U.S. Appl. No. 13/481,087.
Notice of allowance dated Jun. 12, 2014 for U.S. Appl. No. 13/448,061.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 15, 2014 for U.S. Appl. No. 14/037,652.
Notice of allowance dated Oct. 29, 2013 for U.S. Appl. No. 13/204,881.
Notice of allowance dated Dec. 23, 2014 for U.S. Appl. No. 14/007,793.
Office action dated Jan. 15, 2014 for U.S. Appl. No. 13/836,135.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Feb. 14, 2013 for U.S. Appl. No. 13/193,346.
Office action dated Feb. 14, 2013 for U.S. Appl. No. 13/407,408.
Office action dated Feb. 21, 2013 for U.S. Appl. No. 12/047,818.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office action dated Apr. 10, 2014 for U.S. Appl. No. 13/502,989.
Office action dated Apr. 16, 2014 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2014 for U.S. Appl. No. 14/007,793.
Office action dated Jul. 7, 2014 for U.S. Appl. No. 12/535,676.
Office action dated Jul. 15, 2013 for U.S. Appl. No. 13/002,136.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Sep. 9, 2013 for U.S. Appl. No. 13/502,989.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office action dated Oct. 24, 2013 for U.S. Appl. No. 13/313,708.
Office action dated Nov. 7, 2014 for U.S. Appl. No. 12/786,739.
Office action dated Nov. 21, 2014 for U.S. Appl. No. 13/926,822.
Office action dated Nov. 29, 2013 for U.S. Appl. No. 13/193,346.
Office action dated Dec. 10, 2013 for U.S. Appl. No. 13/407,408.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 16, 2013 for U.S. Appl. No. 12/535,676.
Office action dated Dec. 18, 2014 for U.S. Appl. No. 14/037,696.
Office action dated Dec. 19, 2014 for U.S. Appl. No. 13/733,873.
Okahata, et al. Lipid-coated enzymes as efficient catalysts in organic media. Trends in Biotechnology. 1997; 15(2):50-54.
Olivar-Parra, et al. Training referential communicative skills to individuals with autism spectrum disorder: a pilot study. Psychological Reports. 2011; 109:921-939.
Pancrease. Patient information leaflet. Pancrease HL Capsules. Last updated Apr. 30, 2013. Janssen-cilag Ltd. www.medicines.org.uk/EMC/medicine/7326.
Pancreatin 8X USP Powder. Product Specification. Jul. 2000. In: Product Manual. American Laboratories Incorporated. Omaha, NE. p. 1.
Patel, et al. Formulation and evaluation of mucoadhesive glipizide microspheres. AAPS PharmSciTech. 2005; 6(1):E49-E55.
Petrolatum: Pharmaceutical Excipients. London: Pharmaceutical Press. 2006. 1-6.
Roxas, et al. Colds and influenza: a review of diagnosis and conventional, botanical, and nutritional considerations. Alternative Medicine Review. 2007; 12(1):25-48.
Serna, et al. Pathogenesis and treatment of Shiga toxin-producing *Escherichia coli* infections. Curr Opin Gastroenterol. Jan. 2008;24(1):38-47.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Sundstrom, et al. A deadly prion disease: fatal familial insomnia. J Neurosci Nurs. Dec. 2003;35(6):300-5. Abstract only.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
Williams, et al. Intravenous secretin for autism spectrum disorders (ASD). Cochrane Database Syst Rev. Apr. 18, 2012;4:CD003495. doi: 10.1002/14651858.CD003495.pub3.
Xu. Pancreatin therapy in chronic pancreatitis. Clin J Dig, May 2005; 25(5):313-315. (in Chinese with English translation).
U.S. Appl. No. 14/921,896, filed Oct. 23, 2015, Fallon et al.
Block, et al. A rapid food screener to assess fat and fruit and vegetable intake. Am J Prev Med. May 2000;18(4):284-8.

(56) References Cited

OTHER PUBLICATIONS

Borowitz, et al. Study of a novel pancreatic enzyme replacement therapy in pancreatic insufficient subjects with cystic fibrosis. J Pediatr. Nov. 2006;149(5):658-662.

Brinkley, et al. Factor analysis of the aberrant behavior checklist in individuals with autism spectrum disorders. J Autism Dev Disord. Nov. 2007;37(10):1949-59. Epub Dec. 21, 2006.

CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.

Chazalette. A Double-Blind Placebo-Controlled Trial of a Pancreatic Enzyme Formulation (Panzytrat® 25 000) in the Treatment of Impaired Lipid Digestion in Patients with Cystic Fibrosis. Drug Investigation. May 1993; 5(5):274-280. Abstract only.

Creon digestive enzymes. Celic.com/ Jun. 2009. http://www.celiac.com/gluten-free/topic/59195-creon-digestive-enzymes.

Emc, Creon 10000 Capsules, May 18, 2015, Available Online at: www.medicines.org.uk/emc/medicine/2068.

Holten, et al. Appropriate prescribing of oral beta-lactam antibiotics. Am Fam Physician. Aug. 1, 2000;62(3):611-20.

International search report and written opinion dated May 9, 2013 for PCT/US2013/024453.

Notice of allowance dated Sep. 9, 2015 for U.S. Appl. No. 13/193,346.
Notice of allowance dated Nov. 16, 2015 for U.S. Appl. No. 14/493,734.
Notice of allowance dated Dec. 23, 2015 for U.S. Appl. No. 12/493,122.
Office action dated Jan. 15, 2016 for U.S. Appl. No. 13/502,989.
Office action dated Aug. 24, 2015 for U.S. Appl. No. 13/733,873.
Office action dated Aug. 31, 2015 for U.S. Appl. No. 12/535,676.
Office action dated Sep. 8, 2015 for U.S. Appl. No. 11/533,818.
Office action dated Sep. 10, 2015 for U.S. Appl. No. 13/313,629.
Office action dated Sep. 11, 2015 for U.S. Appl. No. 13/313,708.
Office action dated Oct. 30, 2015 for U.S. Appl. No. 14/528,715.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Dec. 10, 2015 for U.S. Appl. No. 13/836,135.
Office action dated Dec. 15, 2015 for U.S. Appl. No. 14/087,930.
Office action dated Dec. 24, 2015 for U.S. Appl. No. 13/757,412.
Office action dated Dec. 24, 2015 for U.S. Appl. No. 14/612,580.

Seltzer, et al. The Symptoms of Autism Spectrum Disorders in Adolescence and Adulthood. Journal of Autism and Developmental Disorders. 2003; 33(6):565-581.

Shelby, et al. Enzymatic debridement with activated whole pancreas. American Journal of Surgery. Oct. 1958; 96(4):545-549.

| | Day After Diagnosis | Protein Urine Level | Fecal Chymotrypsin Level | BP Systolic | BP Diastolic |
|---|---|---|---|---|---|
| Subject 1 | 2 | 4 | 2.2 | 155 | 96 |
| | 4 | 2 | 3 | 130 | 82 |
| | 7 | 0 | 3 | 128 | 78 |
| | 10 | 0 | 6 | 118 | 76 |
| | 15 | 0 | 6.4 | 112 | 76 |
| | 20 | 0 | 6.8 | 114 | 74 |
| | 30 | 0 | 6 | 118 | 72 |
| Subject 2 | 2 | 3 | 4.4 | 168 | 98 |
| | 4 | 3 | 4 | 140 | 86 |
| | 8 | 1 | 7 | 137 | 82 |
| | 12 | 0 | 6.4 | 130 | 78 |
| | 17 | 0 | 8 | 120 | 72 |
| | 22 | 0 | 7.4 | 118 | 70 |
| | 31 | 0 | 7 | 115 | 72 |
| Subject 3 | 2 | 3 | 3.8 | 178 | 120 |
| | 5 | 0 | 6 | 148 | 112 |
| | 7 | 0 | 5.2 | 130 | 100 |
| | 10 | 0 | 7.4 | 122 | 78 |
| | 20 | 0 | 8.8 | 114 | 77 |
| | 35 | 0 | 4.8 | 110 | 78 |
| Subject 4 | 2 | 4 | 0.4 | 155 | 98 |
| | 4 | 3 | 3 | 130 | 90 |
| | 7 | 3 | 4.4 | 124 | 88 |
| | 10 | 3 | 3.8 | 116 | 92 |
| | 16 | 0 | 5.2 | 118 | 82 |
| | 22 | 1 | 6 | 110 | 77 |
| | 31 | 0 | 6.6 | 112 | 77 |
| Subject 5 | 2 | 3 | 6.6 | 176 | 88 |
| | 4 | 3 | 8 | 160 | 82 |
| | 7 | 0 | 8 | 140 | 74 |
| | 10 | 0 | 8.8 | 122 | 72 |
| | 15 | 0 | 6.6 | 120 | 68 |
| | 23 | 0 | 7 | 110 | 66 |
| | 31 | 0 | 8.4 | 100 | 68 |
| Subject 6 | 3 | 4 | 6.6 | 145 | 96 |
| | 5 | 3 | 4.4 | 120 | 82 |
| | 7 | 3 | 8 | 116 | 72 |
| | 12 | 2 | 9.2 | 100 | 74 |
| | 15 | 2 | 8.4 | 108 | 70 |
| | 20 | 0 | 7 | 112 | 72 |
| | 30 | 0 | 7.4 | 110 | 74 |

Figure 4
Measurement of Fecal Chymotrypsin Levels in Preeclamptic Women

| Subject | WEEK 12 | 14 | 16 | 18 | 20 | 22 | 24 | 26 | 28 | 30 | 32 | 34 | 36 | 38 | 40 |
|---|---|---|---|---|---|---|---|---|---|---|---|---|---|---|---|
| 1 | 16.4 | 13 | 14.4 | 15 | 17.4 | 14.4 | 15 | 16.2 | 15.2 | 12.6 | 17.6 | 16 | 16.6 | 17.2 | 16.6 |
| 2 | 26.6 | 24.4 | 22 | 26.8 | 27 | 26.4 | 26.2 | 29 | 27.4 | 26.2 | 29.4 | 23.6 | 27.4 | 26.4 | 28 |
| 3 | 30.2 | 31 | 27.8 | 29 | 28.8 | 30.4 | 29.2 | 28.6 | 29.4 | 27.4 | 26.4 | 29 | 27.6 | 25.4 | 26 |
| 4 | 18 | 19.2 | 14 | 20.2 | 18.8 | 16.8 | 18.4 | 19.6 | 15.6 | 15 | 16.8 | 17 | 15.8 | 16.6 | 17 |
| 5 | 13.4 | 12.8 | 17.4 | 16 | 15 | 15.2 | 16 | 14.8 | 16.2 | 17 | 14.4 | 16 | 13 | 14.4 | 12 |
| 6 | 19 | 17.6 | 18.8 | 18.2 | 19.4 | 18.2 | 18.4 | 19.8 | 20.2 | 6.4 | 5.8 | 3.6 | 3.2 | 4.4 | 3.8 |
| 7 | 30 | 32.6 | 28.8 | 26.6 | 26.4 | 31 | 27.8 | 29.4 | 30.8 | 25.6 | 30 | 26.4 | 30 | 28.4 | 30.8 |
| 8 | 14.2 | 13 | 14.8 | 15.2 | 15 | 17 | 14.8 | 15.6 | 17.4 | 18.8 | 22 | 21.8 | 17.6 | 18.8 | 19 |
| 9 | 19.8 | 24.2 | 22 | 25.4 | 21 | 22.8 | 25.4 | 27.4 | 22 | 25.8 | 23.2 | 19.8 | 20.6 | 26.6 | 24 |
| 10 | 13.2 | 14 | 15.8 | 14.4 | 17 | 15.4 | 13.8 | 12 | 15 | 17.2 | 16 | 16 | 17 | 16.6 | 17 |
| 11 | 22 | 23.2 | 21 | 26 | 26.4 | 19 | 18.8 | 21 | 25.4 | 19 | 24.4 | 18.8 | 22 | 17.8 | 20.2 |
| 12 | 35.6 | 34 | 36 | 30 | 19.8 | 26.6 | 29 | 28.8 | 30 | 31.4 | 28.8 | 19.8 | 28.8 | 31 | 33.45 |
| 13 | 17.8 | 19 | 18.4 | 20.6 | 22 | 21.6 | 18.8 | 19 | 19.8 | 22.8 | 21 | 23.8 | 22 | 20.6 | 21 |
| 14 | 20.8 | 26 | 25.4 | 22 | 20.4 | 19.8 | 22 | 25.2 | 26.4 | 23.8 | 20.6 | 22.2 | 19.8 | 17.6 | 20 |
| 15 | 17.6 | 22 | 18.4 | 22.4 | 23.6 | 19.2 | 24 | 22.6 | 22.8 | 20 | 18 | 19.4 | 23.2 | 18.8 | 23 |
| 16 | 15.6 | 14 | 16.2 | 15.2 | 17 | 16.4 | 18.2 | 16.8 | 16.4 | 19 | 16.2 | 17.4 | 18.8 | 17.2 | 20 |
| 17 | 33 | 29.4 | 31.4 | 30.8 | 29.4 | 28.8 | 29.2 | 30.2 | 33 | 31.6 | 29.6 | 28.4 | 26 | 26.6 | 25 |

METHOD OF TREATING PREGNANCY-INDUCED HYPERTENSION

CROSS-REFERENCE

This application is a divisional application of Ser. No. 14/037,696, filed Sep. 26, 2013, now U.S. Pat. No. 9,023,344, which is a divisional application of Ser. No. 12/047,818, filed Mar. 13, 2008, now U.S. Pat. No. 8,658,163, each of which is incorporated herein by reference in its entirety.

FIELD OF THE INVENTION

The invention relates to a treatment for pregnancy induced hypertension, preeclampsia, eclampsia, toxemia and related disorders of pregnancy, and more particularly, to the use of digestive/pancreatic enzymes in the treatment of pregnancy induced hypertension, preeclampsia, eclampsia and toxemia that may occur during pregnancy.

BACKGROUND OF THE INVENTION

Every year thousands of women suffer from pregnancy induced hypertension. While blood pressure during pregnancy is generally lower than in the non-pregnant state, some pregnant women will develop hypertension. Hypertension during pregnancy can have a significant impact on the mother and the fetus, including, but not limited to stroke or other cardiovascular complications. It is estimated that 7 out of every 100 pregnant women will develop toxemia/eclampsia and/or pre-eclampsia of which hypertension is the main presenting symptom. Mild toxemia, also known as preeclampsia is monitored closely and usually causes few problems for the mother or child. Of note, toxemia, and eclampsia are often used interchangeably to refer to the same condition, and will be used interchangeably throughout the application.

There is no known cause for toxemia. What is known is that toxemia starts to develop as the placenta begins to develop, although the condition may not be detected until the latter part of pregnancy. Most cases of toxemia happen with first pregnancies. Second and subsequent pregnancies are at lower risk, unless the woman is with a new partner. Since there is no known cause of toxemia, there is no way to determine if a woman is at risk for the condition before she gets pregnant.

Preeclampsia causes hypertension and proteinuria, manifesting most often after the twentieth week of pregnancy. In the past, edema was considered a diagnostic criterion. Recently, however, it has been eliminated as a requirement for diagnosis. Preeclampsia causes vasospasm, a condition in which your blood vessels squeeze and then relax almost like a muscle spasm. This causes the smooth lining of the blood vessels to become damaged and rough. Once this damage occurs, the body will send out cells to repair the damage. The cells that arrive first are platelets. As platelets and other blood products try to repair the damage, they form little clots along the blood vessel wall causing the blood vessel to become even more narrow and further decreasing blood flow to the organs. The body continually makes new platelets; however, there is a limited supply of platelets in the body at any one time. Once they have become depleted, spontaneous bleeding can occur.

Other cells passing by the damaged lining of the blood vessels break open, often spilling their toxic contents. These toxic waste products cause high blood pressure and even more damage to other organs. Vasospasm and the miniature blood clots cause further damage by decreasing blood flow and thus decreasing the oxygen supply to vital organs such as the brain, kidneys, and liver.

The term preeclampsia refers to the disease state before a seizure. Once a woman has had a seizure with this disease, it then becomes eclampsia. Eclampsia includes hypertension and proteinuria. Preeclampsia may be classified as mild or severe. Severe preeclampsia is characterized by (1) a systolic blood pressure in a known normotensive woman greater than 140-160 mm Hg or diastolic blood pressure greater than 90-110 mm Hg on 2 occasions at least 6 hours apart in a woman on bed rest and (2) the presence of significant proteinuria. Proteinuria concentration associated with preeclampsia are in the 300 mg/24 hour urine range. Marked proteinuria is defined as 5 g or more of protein in a 24-hour urine collection.

Severe preeclampsia, at times, may be associated with oliguria, cerebral or visual disturbances, pulmonary edema or cyanosis, epigastric or right upper quadrant abdominal pain, impaired liver function, thrombocytopenia, or intrauterine growth restriction. In mild preeclampsia, hypertension and proteinuria are present, but not to these extreme levels, and the patient has no evidence of other organ dysfunction. As preeclapmsia develops into eclampsia/toxemia, oliguria and other symptoms may be present. Many of the health problems associated with eclampsia/toxemia may be very dangerous to the mother and the child, and can result in severe morbidity and potentially mortality for the mother and/or the child. Toxemia may cause liver and /or kidney damage or failure. It may cause problems with eyesight and, if left untreated for too long, may cause the maternal patient to go into seizures. These seizures can lead to coma and even death. Often, the progression of these symptoms cannot be stopped and full blown toxemia occurs, including kidney failure.

The etiology of preeclampsia is still unknown. Many areas have been explored including: the examination of the renin-angiotensin system, selective hormonal examination, including epinephrine, norepinephrine, and vasopressin. Further examination has included endothelin and prostaglandins, all without conclusion or an effective treatment for preeclampsia and the potential resultant eclampsia/toxemia.

Since placental delivery reverses the symptoms of preeclampsia, it suggests that the placenta may have a central role in the condition. Additionally, women with increased placental tissue for gestational age, those with hydatiform moles and/or twin or multiple pregnancies, have an increased prevalence of preeclampsia. This, therefore, leads one to consider the possibility that substances, such as human chorionic gonadotropin, which is high in a hydatiform mole, may be involved. This link between the placenta and the development of preeclampsia is key. As the fertilized ovum begins to divide, it is known as a morula at the sixteen cell stage. As the morula enters the uterine cavity from the fallopian tube, it does not implant until day seven of gestation at which time it is termed a blastocyst. The trophoblastic cells of the blastocyst erode the uterine lining to form large pockets known as lacunae. The trophoblast now forms a divide in the cellular portion and the syncytial portion. The outside covering of the syncytial portion is known as the chorion. The chorion secretes human chorionic gonadotropin which prevents immune attack from the mother, and helps to maintain the corpus luteum of pregnancy until the maternal/fetal exchange can take place through the placenta. This is the beginning of the formation of the placenta.

The cellular trophoblast, once it begins to proliferate without proper changeover to syncytial trophoblastic activity, may cause possible syncytial demise, thus reducing the amount of steroid hormone produced, and also reducing the possibility that the placenta will form correctly. The syncytial trophoblast, known as an extravillous trophoblast. The extravillous trophoblast bores through the endometrium, extending to the decidua and myometrium of the uterus. These extravillous trophoblasts continue their invasion into the spiral arterioles of the uterus and replace the endothelial and muscular linings of the uterine arterioles, leading to vasodilation of the uterine vasculature. This change ensures a continued low resistance system, which potentiates maternal blood flow to the intervillous space and maintains adequate perfusion of the developing fetus.

The mechanism by which the cellular trophoblast is reduced in its proliferation such that the syncytial trophoblast can take over is the presence of proteolytic enzymes, especially that of chymotrypsin. These proteases produced by the mother, especially chymotrypsin, are able to restrain the proliferation of the cellular trophoblast and the overproduction of human chorionic gonadotropin. This mechanism was outlined by Ernest T. Krebs in 1949 (Medical Record, Vol. 162, No. 10, October 1949).

In preeclampsia, the lack of proliferation of the syncytial trophoblasts leads to a lack of extravillous trophoblasts and an improper boring into the muscular lining of the uterine arterioles. This leads to vasospasm of the arteries of the uterine endometrium and results in ischemia, anoxia, necrosis, histamine and tyramine release. With the absence of marked vasodilation and the lumen of the vessels essentially occluded, blood flow and oxygen transfer to the fetus is diminished, leading to the maternal manifestations of preeclampsia as well as the fetal manifestations of oligohydramnios and intrauterine growth restriction (IUGR).

The resultant improper placental development results in placental vascular endothelial dysfunction and a relative uteroplacental insufficiency. The vascular endothelial dysfunction results in increased permeability, hypercoagulability, and diffuse vasospasm.

The loss of protein through the kidney and excretion in the urine and the alterations in the permeability of the vascular system due to the potential endothelial dysfunction results in an increase in vascular permeability. This enhanced vascular permeability ultimately permits the proteins, especially large proteins which are large molecules, to get through the capillaries and the glomerulus of the kidney. This loss of protein creates a potential need for large amounts of protein intake during pregnancy.

With incomplete protein breakdown due to the increased permeability of the vascular system, and its ability to permit large molecules into the vascular system, the protein requirements of the body during pregnancy are even greater than in the non-pregnant state. Further, with the significant loss of protein and the resultant dearth of amino acids present in the pregnant woman, the potential exists for organ dysfunction and potential organ death.

The use of digestive enzymes can facilitate the presence of sufficient protein so as not to allow the body to go into a negative protein balance. This is highly desirable as well as necessary due to the need for proteases such that the body can facilitate formation of the placenta as well as replacement proteins which are lost by the body during the pregnancy.

In view of such findings, there is need for a method of treating those with preeclampsia such that the development of eclampsia/toxemia does not occur in pregnant women. The present invention is directed to therapeutic agents for the treatment of toxemia, preeclampsia and eclampsia and the method for preparing those agents. Further, the present invention is directed to the reduction of the formation of hydatiform moles (molar pregnancies).

More specifically, the present invention relates to stable pharmaceutical preparations containing, but not limited to, digestive/pancreatic enzymes, including, but not limited to, amylases, proteases, cellulase, papaya, papain, bromelain, lipases, chymotrypsin and hydrolases. This combination is made by, but not limited to: direct compression, microencapsulation, lipid encapsulation, wet granulation or other methods including the use of Prosolv®, microencapsulation, lipid encapsulation technology, or other suitable technology. This technology can include the use of rapid dissolution (rapid dissolve), time release or other delivery methods including oral, injection, patch or other method. Further, the delivery of the enzymes can be in the form of a tablet, sprinkles, sachet, capsules, caplets or other compressed tablet delivery, or other oral delivery method.

Further, the invention is directed toward the use of a biomarker, the presence of chymotrypsin in the maternal GI tract to determine the likelihood of developing preeclampsia, pregnancy induced hypertension, and eclampsia/toxemia.

SUMMARY OF THE INVENTION

It is a goal of the present invention to provide a therapeutic agent for the treatment of pregnancy induced hypertension, toxemia, preeclampsia and eclampsia and provide a method for preparing those agents.

Another goal of the present invention is to formulate stable pharmaceutical preparations containing, but not limited to, digestive/pancreatic enzymes including, but not limited to, amylases, proteases, cellulase, papaya, papain, bromelain, lipases, chymotrypsin; and hydrolases.

Yet another goal of the present invention is to make a combination of digestive/pancreatic enzymes is made by but not limited to: direct compression, microencapsulation, lipid encapsulation, wet granulation or other methods including the use of Prosolv®, and other known excipients and additives to accomplish microencapsulation, lipid encapsulation, direct compression, wet or dry granulation or other suitable technology. A further goal of the present invention is to deliver the preparation by means, which can include the use of rapid dissolution (rapid dissolve), time release, or other delivery methods including oral, injection, patch, or other method. Further, the delivery of the enzymes may be in the form of a tablet, capsule, sprinkles, sachet, or other oral delivery method.

An additional goal of the invention is to demonstrate the use of fecal chymotrypsin as a prognosticative indicator of the presence of preeclampsia, eclampsia, toxemia or other disease of pregnancy, or the likelihood of a woman to develop preeclampsia, eclampsia, toxemia, or pregnancy induced hypertension.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION OF THE PREFERRED EMBODIMENT

Since placental delivery reverses the symptoms of preeclampsia, it suggests that the placenta has a central role in the condition. Additionally, women with increased placental tissue for gestational age, or those with hydatiform moles and twin pregnancies, have an increased prevalence of preeclampsia. This leads one to consider the possibility that substances, such as human chorionic gonadotropin, which is present in an increased amount in a hydatiform mole, may be involved. This link between formation of the placenta and the development of preeclampsia is key.

The formation of the syncytial trophoblast, and its secretion of steroid hormones keeps the levels of human chorionic gonadotropin low, and thereby reduces the likelihood of developing preeclampsia. The syncytial trophoblast further proliferates to form a highly specialized trophoblast, known as an extravillous trophoblast. The extravillous trophoblast bores through the endometrium, extending to the decidua and myometrium. These extravillous trophoblasts continue their invasion into the spiral arterioles and replace the endothelial and muscular linings of the uterine arterioles, leading to vasodilation of the uterine vasculature. This change ensures a continued low resistance system, which potentiates maternal blood flow to the intervillous space and maintains adequate perfusion of the developing fetus.

The mechanism by which the cellular trophoblast is reduced in its proliferation so that the syncytial trophoblast may take over is the presence of proteolytic enzymes, especially that of chymotrypsin. The maternal proteases, especially that of chymotrypsin, are able to restrain the proliferation of the cellular trophoblast and the overproduction of human chorionic gonadotropin.

In one embodiment, a stable preparation of digestive/pancreatic enzymes is formed into a dosage formulation containing a therapeutically effective amount of a protease, an amylase, and/or a lipase. The formulation may include additional enzymes, such as pancreatin, chymotrypsin, trypsin, papain and/or papaya. Other combinations of digestive enzymes may also be used. These enzymes can be in the form of animal or plant derivatives, natural or synthetic.

The following outlines a formulary for digestive/pancreatic enzymes for preeclampsia/toxemia:

| |
| --- |
| Amylase 10,000-60,000 U.S.P |
| Protease 10,000-70,000 U.S.P |
| Lipase 4,000-30,000 U.S.P |
| Pancreatin 2,000-6,000 U.S.P |
| Chymotrypsin 2-5 mg |
| Trypsin 60-100 mg |
| Papain 3,000-10,000 USP units/mg |
| Papaya 30-60 mg |

The dosage formulation may be administered by an oral preparation including, but not limited to, an encapsulated tablet, mini-tabs, microcapsule, mini-capsule, time released capsule, sprinkle or other methodology. In one embodiment, the oral preparation is encapsulated using Prosolv technology. Alternatively, the oral preparation may be encapsulated using enteric coating, lipid encapsulation, direct compression, dry granulation, wet granulation, and/or a combination of these methods.

Figure 1:
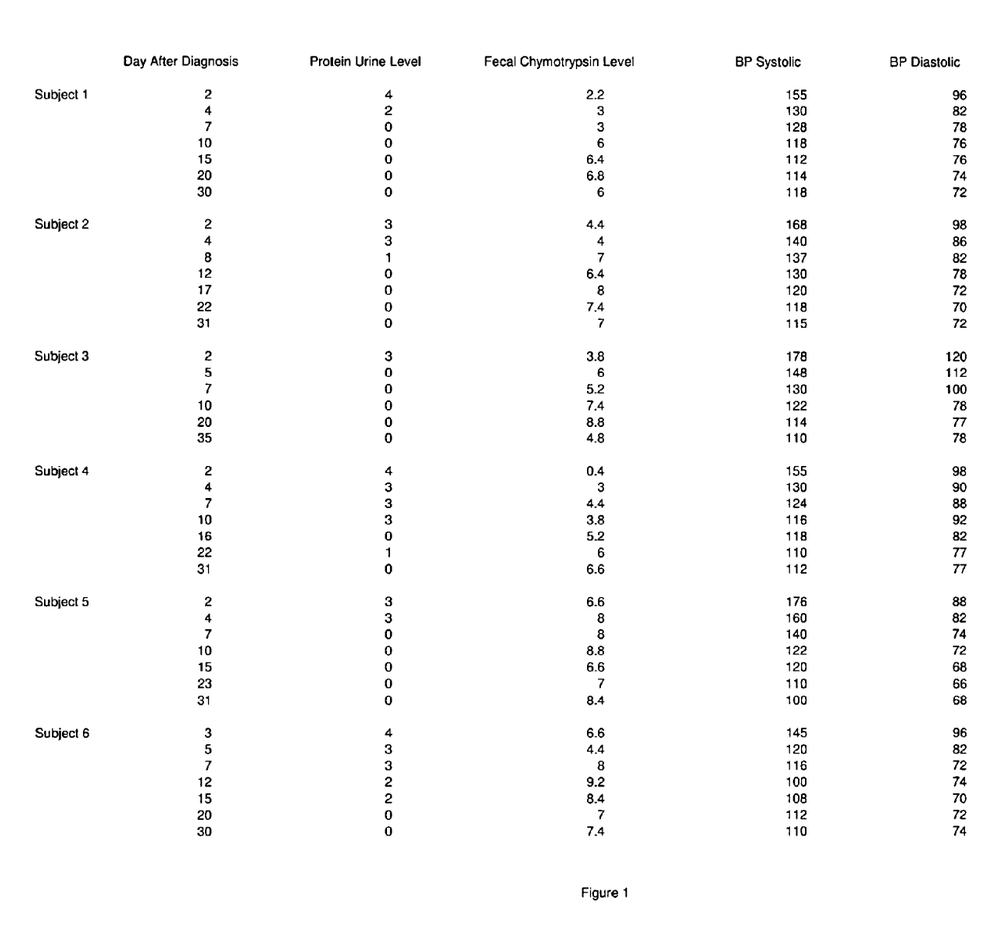
FIG. 1 is a table illustrating the changes in blood pressure, both diastolic and systolic, urine protein level, and fecal chymotrypsin level in pregnant women with preeclampsia that were administered pancreatic enzymes.

In a study conducted by the inventor, six women diagnosed with preeclampsia in weeks 28-34 of pregnancy were examined. Each was administered pancreatic enzymes, including lipases, amylases and proteases, within two days of their diagnosis of preeclampsia for the duration of their pregnancy, while being monitored by their obstetricians. The results of the study are found in FIG. 1, which illustrates the changes in the womens' blood pressure, both diastolic and systolic, urine protein level, and fecal chymotrypsin levels.

Figure 2:
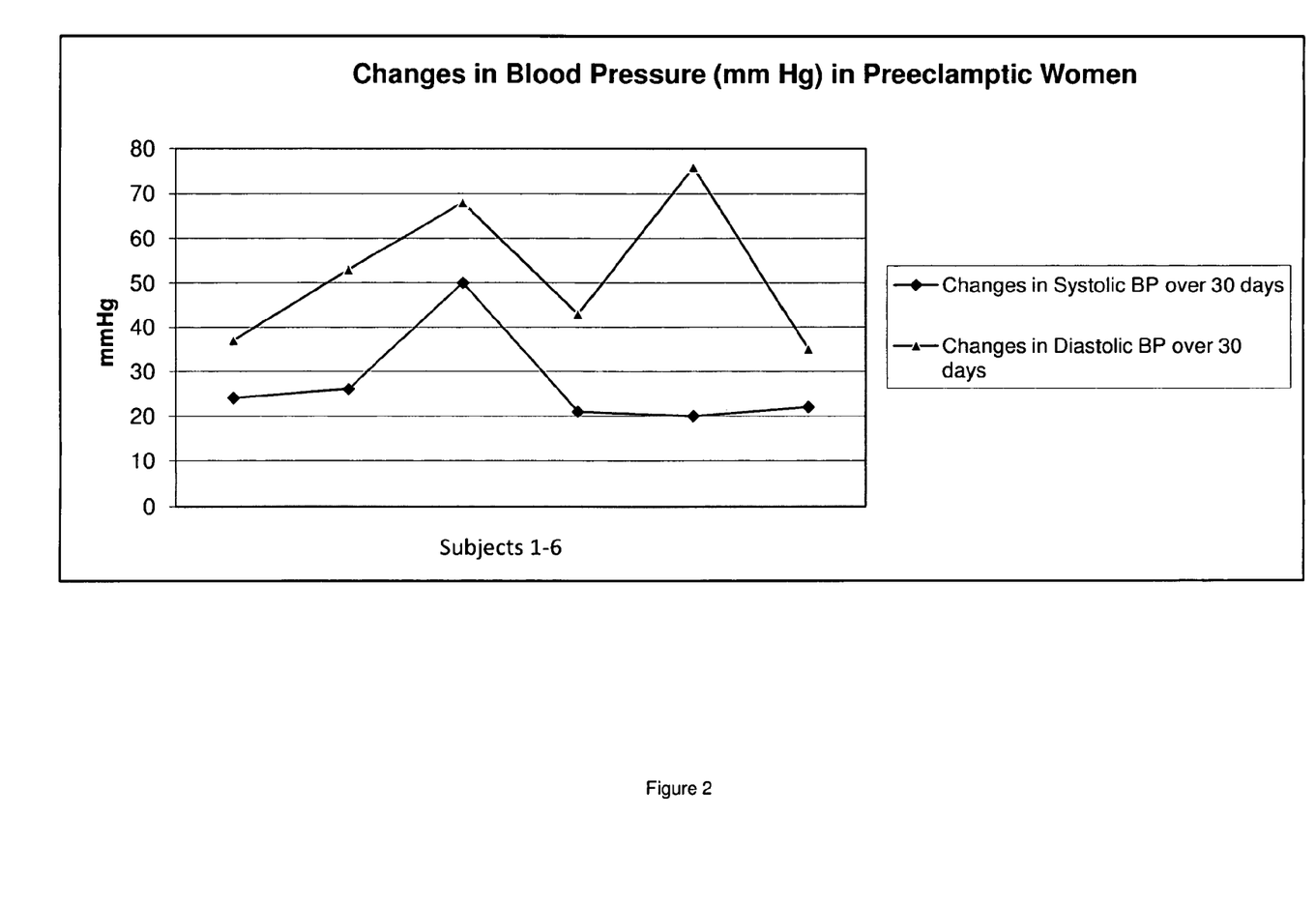
FIG. 2 is a graph illustrating the changes in blood pressure of preeclamptic women over a 30 day period after being administered pancreatic enzymes.

As seen in FIG. 2, it is clear from the results that the blood pressures of the pregnant women were reduced significantly over the 30 days of administration of the pancreatic enzymes. In every case, their blood pressures returned to normal, which is usually 120/80. In some cases, the reversion to a normal blood pressure reading occurred within 15 days.

Figure 3:
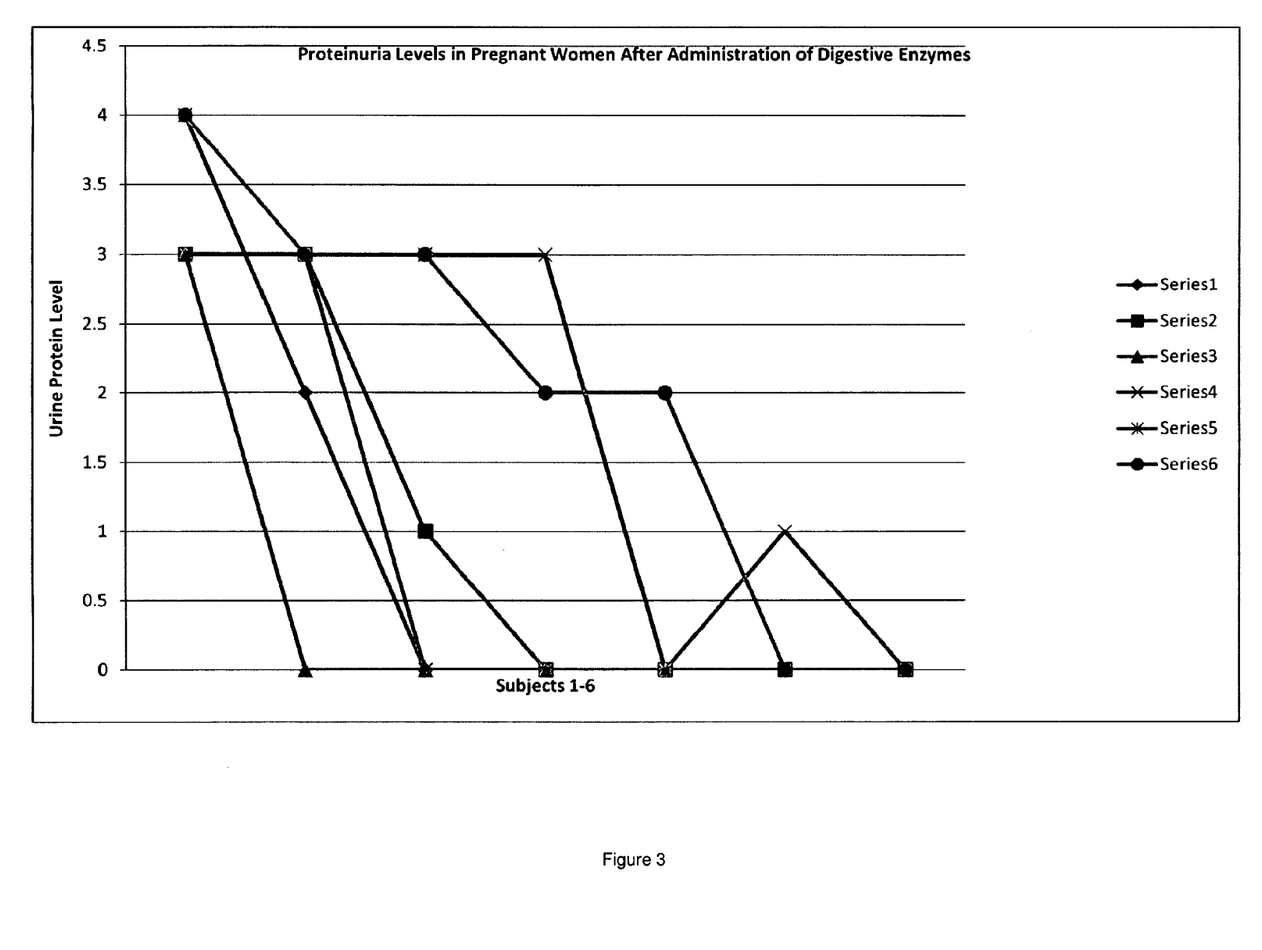
FIG. 3 is a graph illustrating the changes in urine protein level of preeclamptic women over a 30 day period after being administered pancreatic enzymes.

Further, the levels of protein in their urine also reverted to normal within 30-35 days as seen in FIG. 3. Proteinuria is diagnosed by examining the urine through a simple urinalysis. Normal urine has very small amounts of protein present. Larger amounts are usually reported as 1+ to 4+.

Figure 4:
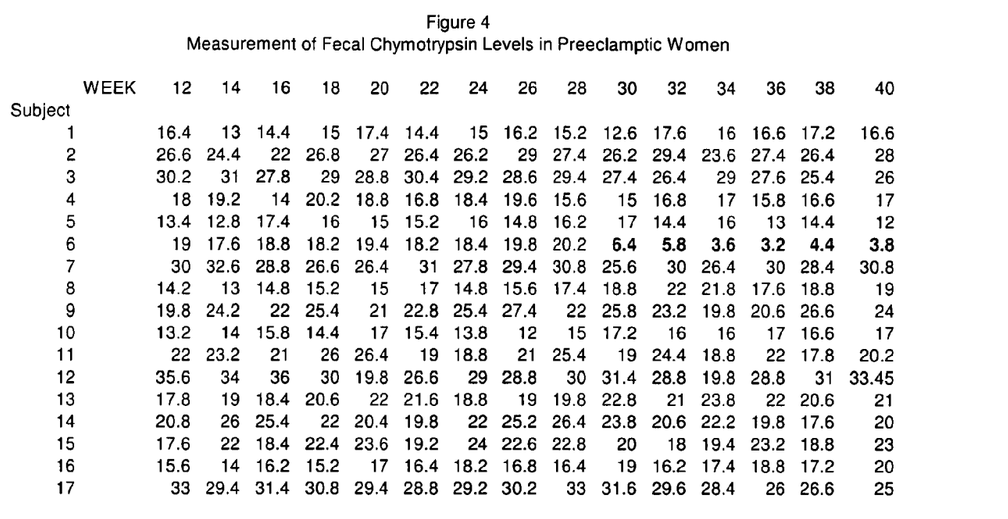
FIG. 4 is a chart illustrating the fecal chymotrypsin levels in seventeen pregnant women from week 12 of pregnancy through week 40 of pregnancy.

In another study, shown in FIG. 4, seventeen women that were pregnant for the first time (primipara) that were in their first trimester were administered a fecal chymotrypsin test every other week from week 12 to week 40 of their pregnancy. One woman, subject 6, developed preeclamptic symptoms, and her fecal chymotrypsin test became abnormal one week prior to the diagnosis of preeclampsia.

Fecal chymotrypsin is a sensitive, specific measure of proteolytic activity. Normal levels of chymotrypsin are considered be greater than 8.4 U/gram. Decreased values (less than 4.2 U/gram) suggest diminished pancreatic output (pancreatic insufficiency), hypoacidity of the stomach or cystic fibrosis. Elevated chymotrypsin values suggest rapid transit time, or less likely, a large output of chymotrypsin from the pancreas.

For the fecal chymotrypsin test, a stool sample was collected from each of the subjects. Each stool sample was analyzed using an enzymatic photospectrometry analysis to determine the level of fecal chymotrypsin in the stool. Alternatively, other methods, such as the colorimetric method, use of substrates, use of assays, and/or any other suitable method may be used to measure the fecal chymotrypsin levels. The levels of fecal chymotrypsin in the samples of the primipara pregnant women were compared to the levels of fecal chymotrypsin in pregnant women not diagnosed with preeclampsia to determine if the primipara pregnant women would benefit from the administration of digestive enzymes.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for treating an individual exhibiting one or more symptoms of pregnancy-induced hypertension, the method comprising administering a therapeutically effective amount of a pharmaceutical preparation comprising digestive enzymes to the individual, wherein the digestive enzymes comprise an amylase, a lipase, a protease, or a combination thereof, whereby pregnancy-induced hypertension is treated.

2. The method of claim 1, wherein the protease comprises chymotrypsin or trypsin.

3. The method of claim 1, wherein the digestive enzymes are provided as pancreatin.

4. The method of claim 1, wherein the digestive enzymes are obtained from a source selected from the group consisting of animal enzymes, plant enzymes, synthetic enzymes, and a combination thereof.

5. The method of claim 1, wherein the pharmaceutical preparation is manufactured using a technology selected from the group consisting of enteric coating, lipid encapsulation, direct compression, dry granulation, wet granulation, and a combination thereof.

6. The method of claim 1, wherein the pharmaceutical preparation is administered orally via a dosage formulation selected from the group consisting of a pill, a tablet, a capsule, a microcapsule, a mini-capsule, a time released capsule, a mini-tab, a sprinkle, and a combination thereof.

7. The method of claim 1, wherein the amount of amylase ranges from 10,000 to 60,000 USP units/dose.

8. The method of claim 1, wherein the amount of protease ranges from 10,000 to 70,000 USP units/dose.

9. The method of claim 1, wherein the amount of lipase ranges from 4,000 to 30,000 USP units/dose.

10. The method of claim 3, wherein the amount of pancreatin ranges from 2,000 to 6,000 USP units/mg units/dose.

11. The method of claim 2, wherein the amount of chymotrypsin ranges from 2 to 5 mg/dose.

12. The method of claim 2, wherein the amount of trypsin ranges from 60 to 100 mg/dose.

\* \* \* \* \*